United States Patent
Larcom et al.

(10) Patent No.: US 6,585,676 B1
(45) Date of Patent: Jul. 1, 2003

(54) UVC RADIATION THERAPY FOR CHRONIC LYMPHOCYTIC LEUKEMIA

(75) Inventors: Lyndon L. Larcom, Clemson, SC (US); Amy Tuck, Piedmont, SC (US); Samuel Smith, Greenville, SC (US)

(73) Assignee: Clemson University, Clemson, SC (US)

( * ) Notice: Subject to any disclaimer, the term of this patent is extended or adjusted under 35 U.S.C. 154(b) by 10 days.

(21) Appl. No.: 09/857,982
(22) PCT Filed: Apr. 19, 2001
(86) PCT No.: PCT/US01/12731
§ 371 (c)(1),
(2), (4) Date: Jun. 12, 2001
(87) PCT Pub. No.: WO01/80939
PCT Pub. Date: Nov. 1, 2001

Related U.S. Application Data (60) Provisional application No. 60/198,296, filed on Apr. 19, 2000.

(51) Int. Cl.$^7$ ............................................... A61M 37/00
(52) U.S. Cl. ..................... 604/4.01; 604/6.01; 604/6.08
(58) Field of Search ............................... 604/6.08, 6.01, 604/4.01

(56) References Cited

U.S. PATENT DOCUMENTS

| | | | | |
|---|---|---|---|---|
| 4,428,744 A | * | 1/1984 | Edelson | 128/DIG. 3 |
| 4,573,960 A | * | 3/1986 | Goss | 604/6.08 |
| 4,613,322 A | | 9/1986 | Edelson | |
| 5,147,289 A | * | 9/1992 | Edelson | 424/278.1 |
| 5,871,459 A | | 2/1999 | Muller | |
| 5,980,954 A | * | 11/1999 | Bolton | 422/24 |
| 5,984,887 A | * | 11/1999 | McLaughlin et al. | 604/6.08 |
| 6,190,608 B1 | | 2/2001 | Laub et al. | |
| 6,193,681 B1 | * | 2/2001 | Davidner et al. | 205/435 |

OTHER PUBLICATIONS

US/ISA, International Search Report, Oct. 18, 2001; US PCT/US01/12731, 3 pages.

Bartik, Mary M.; Welker, Debra & Kay, Neil E.; "Impairments in Immune Cell Function in B Cell Chronic Lymphocytic Leukemia", Seminars in Oncology, vol. 25, No. 1: pp 27–33, Feb. 1998; US.

Byrd, John C.; Rai, Kanti R.; Sausville, Edward A.; & Grever, Michael R.; "Old and New Therapies in Chronic Lymphocytic Leukemia: Now is the Time for a Reassessment of Therapeutic Goals," Seminars in Oncology, vol. 25, No. 1: pp. 65–74, Feb., 1998, US.

Byrd, Flinn & Grever, Guest Editors, "Introduction", Seminars in Onvology, vol. 25, No. 1: pp 4–5, Feb., 1998, US.

(List continued on next page.)

Primary Examiner—William C. Doerrler
Assistant Examiner—Filip Zec
(74) Attorney, Agent, or Firm—Dority & Manning, PA (57) ABSTRACT

Lymphocytes from chronic lymphocytic leukemia (CLL) patients have been found to be readily killed by ultra-violet light-C (UVC) radiation. Cells from healthy donors were minimally affected by doses of UVC 10 times higher than those which caused dramatic drops in the metabolism of CLL cells and eventual death.

Irradiated cells from CLL patients and from healthy individuals all demonstrated a number of single strand DNA breaks and alkali-labile sites compared to unirradiated control cells. The extent of DNA damage to both healthy and CLL cells is dose dependent. However, the CLL cells demonstrated more extensive DNA fragmentation and an inability to undergo self-repair. The heightened sensitivity to UVC radiation of lymphocytes from CLL patients is used to provide an excorporeal treatment of CLL lymphocytes followed by the re-introduction of the treated lymphocytes to the patient.

12 Claims, 10 Drawing Sheets

MTT Response of CLL B & T lymphocyte populations after UVC irradiation. CLL cells were isolated and separated with magnetic beads. The cells were irradiated in PBS and suspended in 15% autologous plasma TCM for incubation. The MTT response was measured after 4 hours. ROD=Relative Optical Density. Data for 3 CLL patients.

OTHER PUBLICATIONS

Wieslthier, Janet S.; Rothstein, Thomas L.; Yu, Thomas L.; Anderson, Tom; Japowicz, Mary C.; & Koh, Howard K.; "Inefficacy of Extracorporeal Photochemotherapy in the Treatment of B–Cell Chronic Lymphocytic Leukemia: Preliminary Results", American Journal of Hematology 41:123–127 1992, US.

Pass, Harvey I., "Photodynamic Therapy in Oncology: Mechanisms and Clinical Use," Journal of the National Cancer Institute, vol. 85, No. 6, pp 443–456, Mar. 17, 1993, US.

Reed, John C., "Molecular Biology of Chronic Luymphocytic Leukemia," Seminars in Oncology, Vo. 25, No. 1: pp 11–18, Feb., 1998, US.

Tuck, Amy; Smith, Samuel; Whitesides, John F.; & Larcom, Lyndon; "Hypersensitivity of Lymphocytes from Chronic Lymphocytic Leukemia Patients to Ultraviolet Light–C Radiation", Leukemia and Lymphoma, vol. 36(1–2) pp 169–177, 1999, Malaysia.

* cited by examiner

Percent Trypan Blue Positive CLL and Healthy Lymphocytes after UVC Irradiation

| Dose (J/m$^2$) | 4 hours CLL | 24 hours CLL | 48 hours CLL | 4 hours Healthy | 24 hours Healthy | 48 hours Healthy |
|---|---|---|---|---|---|---|
| 0 | 3.0 ± 0.7 | 9.3 ± 2.1 | 21.1 ± 4.8 | 2.8 ± 0.9 | 2.7 ± 0.5 | 4.2 ± 1.1 |
| 2 | 1.0 ± 0.0 | 9.7 ± 5.7 | 31.3 ± 10.9 | - | - | - |
| 4 | 1.8 ± 0.4 | 18.7 ± 2.3 | 43.1 ± 4.1 | 1.2 ± 0.5 | 2.3 ± 1.0 | 3.8 ± 1.1 |
| 8 | 2.9 ± 0.7 | 22.3 ± 1.5 | 47.0 ± 2.4 | 1.7 ± 0.5 | 3.2 ± 1.1 | 4.2 ± 1.4 |
| 16 | 2.4 ± 0.7 | 26.2 ± 3.1 | 50.2 ± 2.1 | 2.2 ± 0.9 | 4.5 ± 2.3 | 9.8 ± 6.0 |
| 24 | 0.8 ± 0.4 | 23.7 ± 4.9 | 44.8 ± 4.2 | 1.3 ± 0.3 | 1.0 ± 0.6 | 1.3 ± 0.3 |
| 32 | 1.0 ± 0.6 | 19.0 ± 4.0 | 39.7 ± 8.9 | - | - | 4.0 ± 2.0 |
| 40 | 0.7 ± 0.7 | 20.7 ± 4.8 | 49.0 ± 2.6 | - | - | - |

FIG 1

CLL and healthy lymphocytes were suspended in PBS for irradiation with UVC. The cells were incubated in 15% autologous plasma TCM. MTT response was measured after 4 hours (a) and 24 hours (b). ROD = Relative optical density. Data for 8 CLL patients and 3 healthy controls at 4 hours post irradiation; 4 CLL patients and 3 healthy controls at 24 hours

FIG 2

DNA damage of CLL lymphocytes after UVC irradiation measured by the comet assay. CLL lymphocytes were irradiated in PBS and incubated in 15% autologous plasma TCM. After 1 hour incubation, the comet assay was run. Data for 10 CLL patients.

FIG 3

DNA damage of healthy lymphocytes after UVC Irradiation measured by the comet assay. Healthy lymphocytes were irradiated in PBS and incubated in 15% autologous plasma TCM. After 1 hour incubation, the comet assay was run. Data for 9 healthy controls.

FIG 4

Changes in NAD concentrations of CLL and healthy lymphocytes after UVC irradiation. CLL and healthy cells were irradiated in PBS and incubated in 15% autologous plasma TCM for 0, 1, 2, 3, & 4 hours. At the indicated times, NAD was extracted and measured using the NAD enzyme cycling assay. a) 5 healthy controls b) 8 CLL patients.

FIG 5

Cell death analysis of a CLL patient's lymphocytes after UVC irradiation. Cells were irradiated in PBS and incubated in 15% autologous plasma TCM for 48 hours and stained with annexin V and PI. The cells were examined by flow cytometry.

FIG 6

Cell death analysis of healthy lymphocytes after UVC irradiation. Healthy lymphocytes were suspended in PBS for irradiation with UVC. The cells were incubated in 15% autologous plasma TCM for 48 hours. They were then stained with annexin V and PI and examined by flow cytometry. Data for 4 healthy controls.

FIG 7

Kinetics of cell death for CLL and healthy lymphocytes after UVC irradiation. Cells were irradiated in PBS and incubated in 15% autologous plasma TCM for the indicated times and then stained with annexin V and PI. The cells were examined by flow cytometry. Data for 7 CLL patients (a) and 4 healthy controls (b).

FIG 8

MTT Response of CLL B & T lymphocyte populations after UVC irradiation. CLL cells were isolated and separated with magnetic beads. The cells were irradiated in PBS and suspended in 15% autologous plasma TCM for incubation. The MTT response was measured after 4 hours. ROD=Relative Optical Density. Data for 3 CLL patients.

UVC RADIATION THERAPY FOR CHRONIC LYMPHOCYTIC LEUKEMIA

RELATED APPLICATIONS

This application claims the benefit of U.S. application Ser. No. 60/198,296 filed on Apr. 19, 2000, and which is incorporated herein by reference.

FIELD OF THE INVENTION

This invention is directed towards a therapeutic treatment for chronic lymphocytic leukemia. The lymphocytes from CLL patients have been found to be sensitive to ultraviolet radiation in the UVC range. It has been found possible to provide a UVC radiation exposure which will kill CLL cells without any measurable adverse effects on healthy lymphocytes taken from non-leukemia control patients. A treatment therapy in which a CLL patient's blood is treated extracorporeally with UVC radiation is provided which takes advantage of the CLL lymphocyte's sensitivity to UVC radiation.

BACKGROUND OF THE INVENTION

Chronic lymphocytic leukemia (CLL) is a hematological malignancy characterized by the clonal expansion of naïve B-lymphocytes mainly in G0 phase of the cell cycle. CLL results in the accumulation of mature immunologically defective lymphocytes in the G0 phase. The disease is further characterized by the accumulation of B-lymphocytes in bone marrow, lymph nodes, spleen, and liver. In CLL patients, both the B and T cells are ineffective in their response to antigens and are associated with hypogammaglobulinemia and susceptibility to infectious diseases. The end stages of the disease results in the failure of production of myeloid and erythroid marrow elements as well as the presence of lymphoid masses. It is currently believed that the defective lymphocytes in CLL patients are produced at a normal rate as in healthy individuals, but fail to undergo appropriate apoptosis.

Currently, existing therapies and treatment protocols for advanced clinical stages have met with only partial success. Traditional drug treatments have involved combinations of chlorambucil (an alkylating agent) and prednisone (corticoid steroid). More recently, the purine analog fludarabine has been shown to have positive effects on new and pre-treated CLL patients. However, such drug treatments pose undesirable side effect for some patients. Further, some patients develop resistance to a particular drug.

The use of UVA radiation in an extracorporeal photo chemotherapy has been tested in CLL patients and has brought about improvements in T-cell lymphoma patients, but showed no clinical effect in CLL patients. (Wieselthier, J. S. et al Inefficacy of Extracorporeal Phytochemotherapy in the Treatment of T-cell Chronic Lymphocytic Leukemia: Preliminary Results. *American Journal of Hematology*, 41, 123–127 (1992) and (Edelson, R. L. "Photopheresis: A Clinically Relevant Immunobiologic Response Modifier" *ANN NY Sciences*, Vol. 636 p. 154–164 (1991)) and which are both incorporated herein by reference.

Accordingly, there remains room for variation and improvements with respect to therapies and treatments for CLL.

SUMMARY OF THE INVENTION

It has now been discovered that a therapeutic treatment to CLL patients may offer improved efficiencies in alleviating symptoms and offer a useful therapeutic tool in minimizing the onset and severity of symptoms. In so doing, it is possible to avoid chemical drug treatments which may have adverse effects and for which the body may develop resistance In one aspect, the invention resides in a method of treating lymphcytes of CLL patients so as to preclude population accumulation of naïve B-lymphcytes. The use of UVC radiation of the affected population of lymphocytic cells has been found to bring about the cell death of the targeted population of cells through a combination of apoptosis and cell necrosis. In yet another aspect of this invention, it has been found that the levels of UVC radiation needed to bring about the death of the target population of lymphocytic cells is approximately 10% the level required to bring about deleterious effects on healthy lymphocytic cells.

In a further aspect, the present invention resides in a process of treating a CLL patient by removing a portion of a patient's blood supply; separating the blood supply into a fraction enriched with lymphocytes; exposing the lymphocyte-enriched fraction to UVC radiation; and, returning the treated fraction and untreated fractions to the patient.

These and other features, aspects, and advantages of the present invention will become better understood with reference to the following description and appended claims.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings.

DESCRIPTION OF THE PREFERRED EMBODIMENT

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

In describing the various figures herein, the same reference numbers are used throughout to describe the same material, apparatus or process pathway. To avoid redundancy, detailed descriptions of much of the apparatus once described in relation to a figure is not repeated in the descriptions of subsequent figures, although such apparatus or process is labeled with the same reference numbers.

In accordance with this invention, it has been shown that CLL lymphocytes may be killed using does of UVC radiation substantially lower than those needed to kill or damage healthy lymphcytes. The UVC radiation induces damage at the DNA level by the production of photo lesions that are normally excised by the nucleotide excision repair (NER) system. Using an alkaline comet assay, it has been demonstrated that only limited repair of the UV-induced lesions occurs in the treated CLL cells. In contrast, treated cells from healthy individuals undergo a repair process which is essentially complete within about four hours.

While not wishing to be limited by theory, it is Applicant's belief that the lymphocytes from CLL patients are defective in their ability to regulate utilization and/or synthesis of AND and ATP following DNA damage. Lymphocytes in general are associated with low levels of deoxyribonucleotide pools. The NER process is enhanced when deoxyribonucleosides are added to the medium. This theory is consistent with the observation that the noted defect is consistent with the failure of the CLL cells to undergo a normal apoptosis clearing.

Set forth in the example which follows is the experimental data which establishes the sensitivity of CLL lymphocytes to low exposures of UVC radiation. The techniques used and commented on below are well known to one having ordinary skill in the art. Additional information on the experimental protocols may be found in reference to preliminary investigation results reported in a publication by co-inventor Amy Tuck entitled, "The Sensitivity of Chronic Lymphocytic Leukemia Lymphocytes to Ultra-Violet Light -C Due to DNA Repair Defects", dissertation, Clemson University Graduate School, Clemson, S.C., submitted August, 1999, and which is incorporated herein by reference.

Cell Isolation and Culture

Lymphocytes from CLL patients and healthy donors were isolated from whole blood on histopaque gradients. The isolated cells were washed in phosphate-buffered saline, pH 7.4 (PBS) and were thereafter suspended in RPMI 1640 medium supplemented with 15% autologous plasma and 1% gentamycin and incubated at 37° C. in an atmosphere of 5% $CO_2$. The cells were irradiated in 1 ml increments at a rate of 1 W/m$^2$. The UVC light source was a germicidal lamp having a maximum intensity at 254 nm.

Lymphocyte Separation

Healthy B-cells were selected from the washed mononuclear cell population using immunomagnetic polystyrene Dynabeads M450 Pan-B CD 19 (Dynel, Inc.) with the T-cells remaining in suspension. The CLL T-lymphocytes were selected from the lymphocyte population using Dynabeads M450 CD 4 and CD 8. The purities of the B and T cell populations were measured by flow cytometry using a two color immuno fluorescent agent protocol.

Assay for Cellular Metabolism

Cellular metabolism was measured by the conversion of 3-(4-5-dimethylthiazol-2-yl)-2,5-diphenyl tetrazolium bromide (MTT) to a blue formazan dye or the similar compound of MTS. Following standard incubation assays using the above reagents, absorbance values at appropriate wavelengths were made.

For instance, a sample of $2 \times 10^5$ cells in a volume of 100 µl was placed in each well of a 96 well plate along with 25 µl of a solution of 5 mg/ml MTT. The plates were incubated for four hours at 37° C. and 5% $CO_2$. A lysing solution was then added to each of the wells followed by reading the plate 24 hours later at 540 nm.

Apoptosis Detection

Cell populations were washed in 0.5 ml PBS and then resuspended in 200 µl Annexin V binding buffer (Caltag). 1 µg/test of Annexin V was added for apoptosis detection and the solution was allowed to incubate at room temperature for 10 minutes. At least 10,000 cells per tube that fell within the predetermined leukocyte gate were collected in listmode for subsequent analysis. Samples are analyzed on an EPICS 751-flow cytometer with the 488 nm line (300 mw) of an argon ion laser (Model I-90, Coherent) and Clyclops analysis software.

Comet Assay

Cells were incubated for at least one hour to allow the incision step of DNA repair to take place. The cells were then washed and suspended in PBS. $2 \times 10^4$ cells were mixed with 0.75% low melting point agarose and placed on a base layer of 1.2% normal melting point agarose on a frosted slide. A cover slip was placed on top and the agarose was allowed to gel on ice for 10 minutes. Following removal of the cover slip, a final layer of 0.5% low melting point agarose was placed on top of the second gel layer and the slide was cooled on ice for 10 minutes. The slide was then immersed in a cold lysing solution at 4° C. for a minimum of 1 hour. Next, the slide was soaked in electrophoresis buffer for 20 minutes and electrophoresed at 18 volts and 300 mA for 24 minutes. Following electrophoresis, the slide/cells were washed and stained with propidium iodide for 10 minutes. The propidium iodide (PI) stained comets were examined using inverted fluorescence microscopy and classified into stages as set forth in the accompanying figures.

NAD Enzyme Cycling Assay

The NAD was extracted from cells at the indicated times by boiling in 0.3 mls of 0.1 molar HCl for 5 minutes. The samples were cooled and centrifuged at 2,000 g for 10 minutes. The supernatant was neutralized with 0.1 molar NaOH and re-centrifuged at 10,000 g for 10 minutes and then stored on ice. The enzyme assay was carried out in low light due to light sensitivity of phenazine ethosulfate (PES). Equal volumes of 1.0 M Tricine-NaOH buffer (pH 8.0) and 16.6 mM PES, 4.2 mM 3-(4,5-dimethyl thiazol-2-yl)2,5-diphenyl tetrazolium bromide (MTT), 40 mM $Na_2$ EDTA, and 5.0 M ethanol were mixed immediately before the assay and 100 µl were placed in each well of a flat bottom 96 well plate. A standard curve was obtained by taking appropriate volumes of NAD which were added to the wells and the volume in each well was brought to 180 µl with 0.1 M NaCl. The plate was incubated at 37° C. for 5 minutes. Alcohol dehydrogenase in a concentration of 100 units/ml in 0.1 M Tricine-NaOH was prepared fresh and a volume of 20 µl was added to each well to start the reaction. Following an incubation of 40 minutes at 37° C., absorbance was read at 595 nm using a microplate reader.

Data Analysis

Data presented in each figure and table were averaged for the indicated number of donors. The readings obtained for each donor were normalized so that the results obtained from different donors could be compared. The NAD concentrations were determined by generating a standard curve. These were then normalized to the concentrations obtained for control cells (unirradiated cells at time 0). Measurements were normalized to the control sample (unirradiated cells) in each experiment. Results are presented as mean ± standard error of the mean.

Extracorporeal UVC Treatment

A variety of suitable methods and apparatuses for exposing blood and blood components to UV light are known within the art. For instance, U.S. Pat. No. 5,871,459 to Miller, U.S. Pat. No. 4,613,322 to Edelson, and U.S. Pat. No. 6,190,608 B1, which are all incorporated herein by reference, are directed to extracorporeal UV irradiation of blood components.

For instance, conventional continuous or batch type centrifuge devices may be used to isolate and enrich fractions of a patient's blood. Further, the centrifuge may be used to isolate a fraction enriched in lymphocytes. The red blood cells may be returned to the patient along with a majority of the blood plasma while the concentrated lymphocytic fraction is delivered to any one of several types of known irradiation stations.

When combined with a continuous centrifuge, it is possible that between 25 to 75% of a patient's blood lymphocytes may be isolated in a volume of about 250 to 750 ml and contained in a minor proportion of plasma. The patient's outflow of red blood cells and plasma is returned on a continuous basis to the patient. In this manner, a large proportion of the patient's total lymphocytes may be treated. Following treatment, the irradiated flow of the enriched lymphocyte fraction can be returned to the patient.

It is noted, however, that it may be desirable to treat only about 10% of a patient's total lymphocytes at any one treatment to minimize risks associated with adverse reactions associated with cell necrosis of the UVC treated lymphocytes. An optimal volume/percentage of lymphocytes treated for any individual patient may be readily determined by routine experimentation.

While not separately set forth herein, Applicant's investigation has revealed that following UVC exposure to lymphocytes from CLL patients, partial recovery of the treated cells can be achieved through supplementation of media with an external source of deoxyribonuclesides. Accordingly, medium used to suspend the lymphocytes during or following UVC treatment should not be supplemented with nucleosides.

Figure 1:
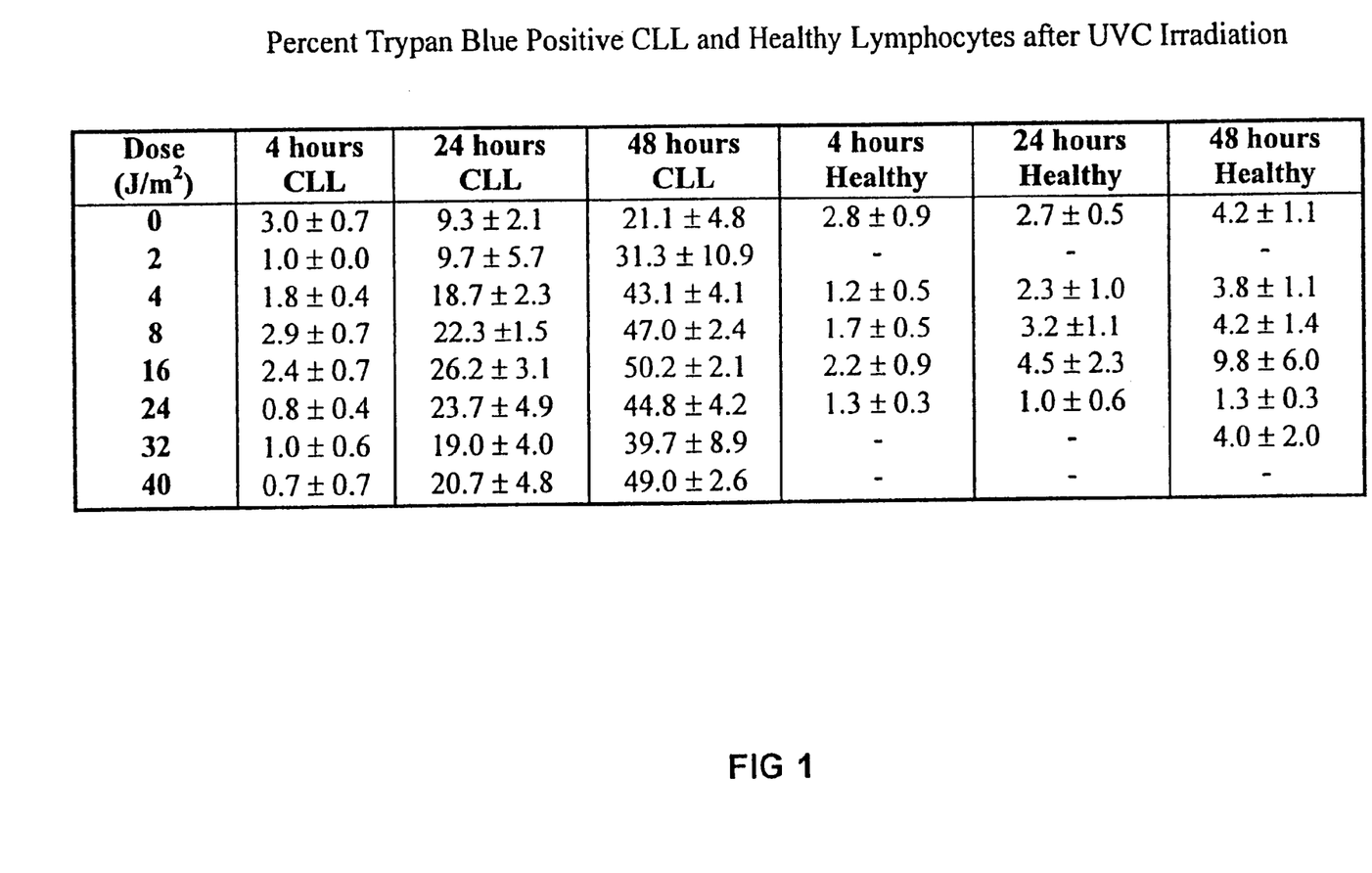
FIG. 1 sets forth a per cent of Trypan blue positive CLL and healthy lymphocytes following UVC radiation.

The effects of the UVC irradiation on CLL and healthy lymphocytes may be seen in reference to FIG. 1. As set forth in FIG. 1, the UVC treatment induced a significant cell death in CLL cells as indicated by the increase in Trypan blue positive cells. As noted in FIG. 1, at the 24 hour and 48 hour intervals there is a significant increase in cell death above unirradiated controls for UVC doses ranging from 2 to 16 $J/m^2$. The data set forth in FIG. 1 identifies the CLL lymphocytes as being susceptible to low doses of UVC irradiation. In comparison, the healthy lymphocytes are largely unaffected.

Figure 2:
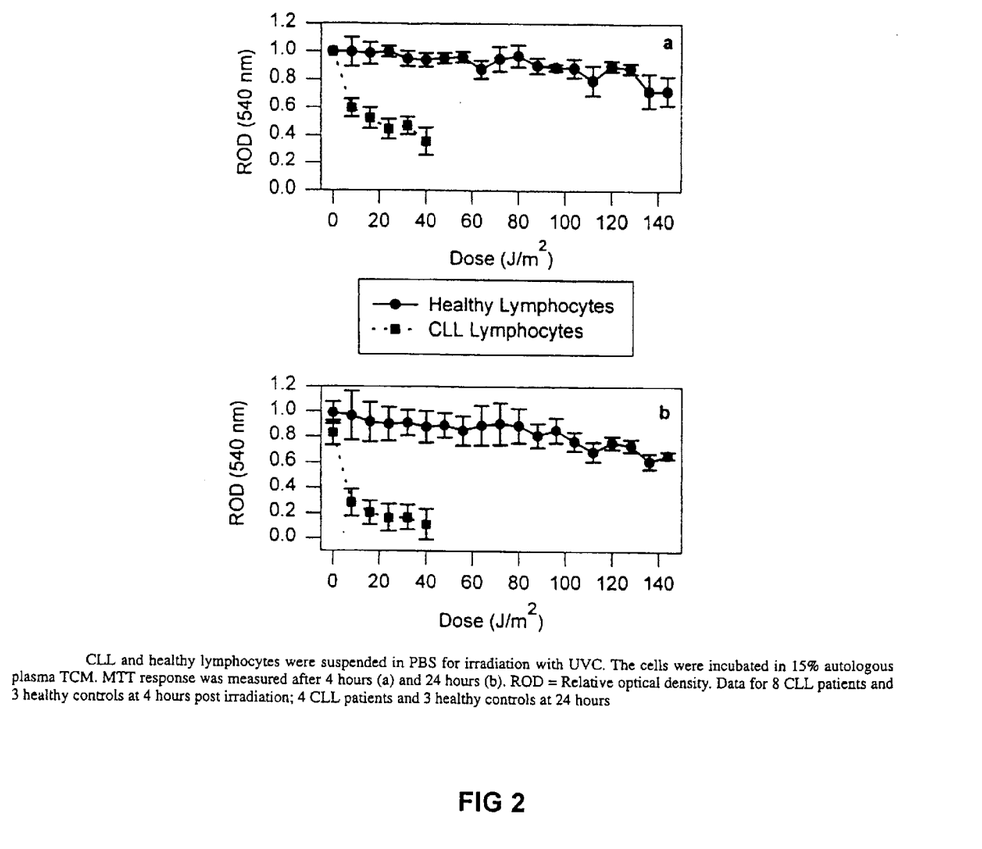
FIG. 2 is comparative graphs of CLL and healthy lymphocytes following irradiation with UVC. The MTT response was measured after 4 hours (a) using 8 CLL patients and 3 healthy control individuals and at 24 hours (b) for 4 CLL patients and 3 healthy control individuals.

As set forth in reference to FIG. 2 UVC irradiation brings about a pronounced effect on cellular metabolism for CLL lymphocytes as measured by reduction of MTT. For CLL lymphocytes, the UVC irradiation produced a dramatic decrease in cellular metabolism. The optical density for cells exposed to 40 $J/m^2$ was 40 to 60% lower than that for unirradiated controls when measured 4 hours after irradiation. This trend continued over 24 hours resulting in a 70 to 80% decrease in absorbance relative to untreated controls. In contrast, after 4 hours following UVC exposure, minimal effects on cells isolated from healthy donors were noted. The minimal effects were noted following UVC doses almost 10 times as great as the exposure levels which caused a significant metabolic drop for CLL cells. While not separately reported, similar effects were noted on other tetrazolium salts MTS and XTT. While the reduction methods may differ for the various salts, all require the presence of NAD(P)H for reduction to take place, thereby indicating a drop in reduced pyridine nucleotides following UVC radiation. The healthy cells did not have a corresponding drop in absorbance as seen in the CLL cell response.

Figure 3:
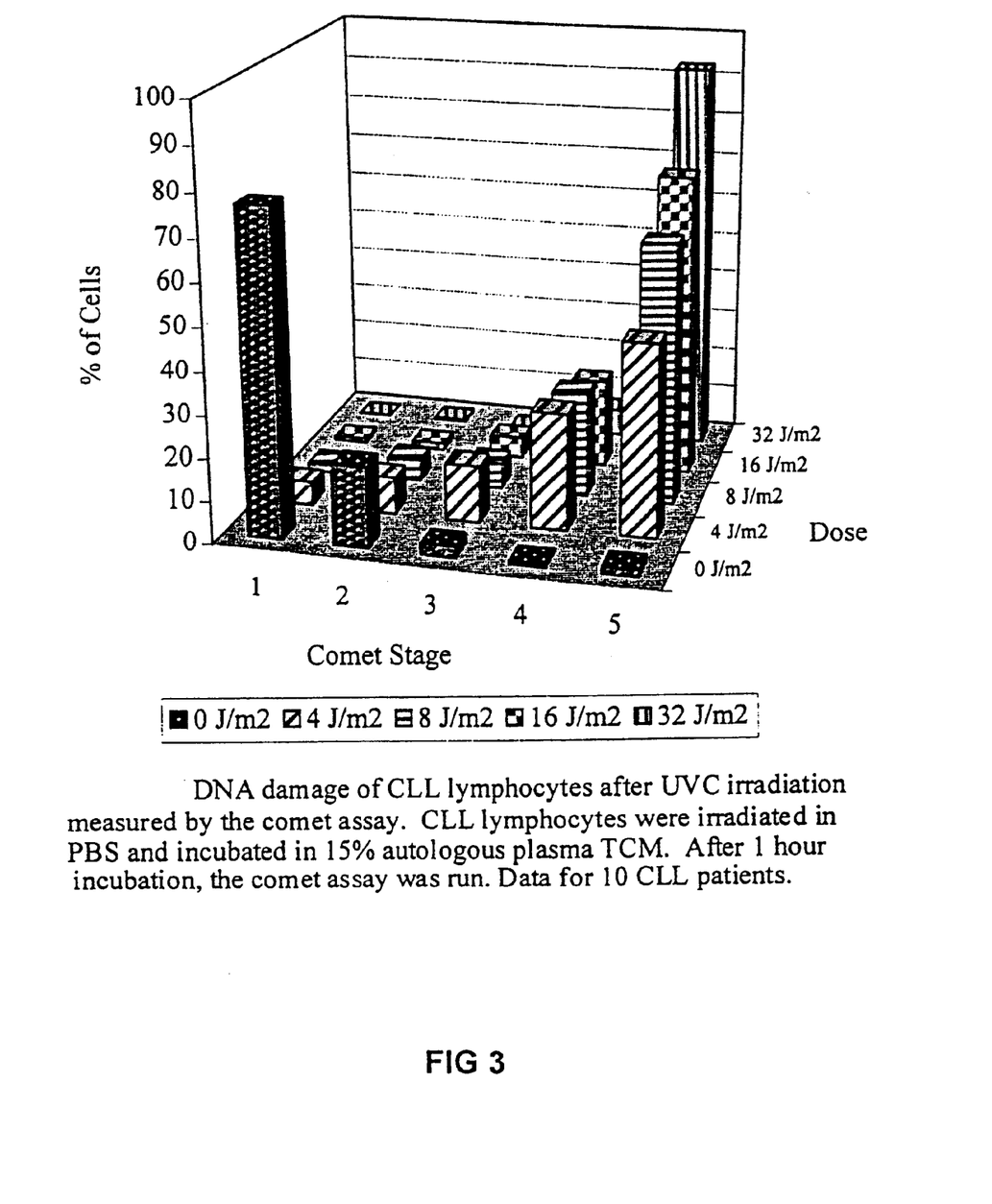
FIGS. 3 and 4 are graphs correlating DNA damage of CLL and healthy lymphocytes following UVC irradiation and an 1 hour incubation as measured by the comet assay.
Figure 4:
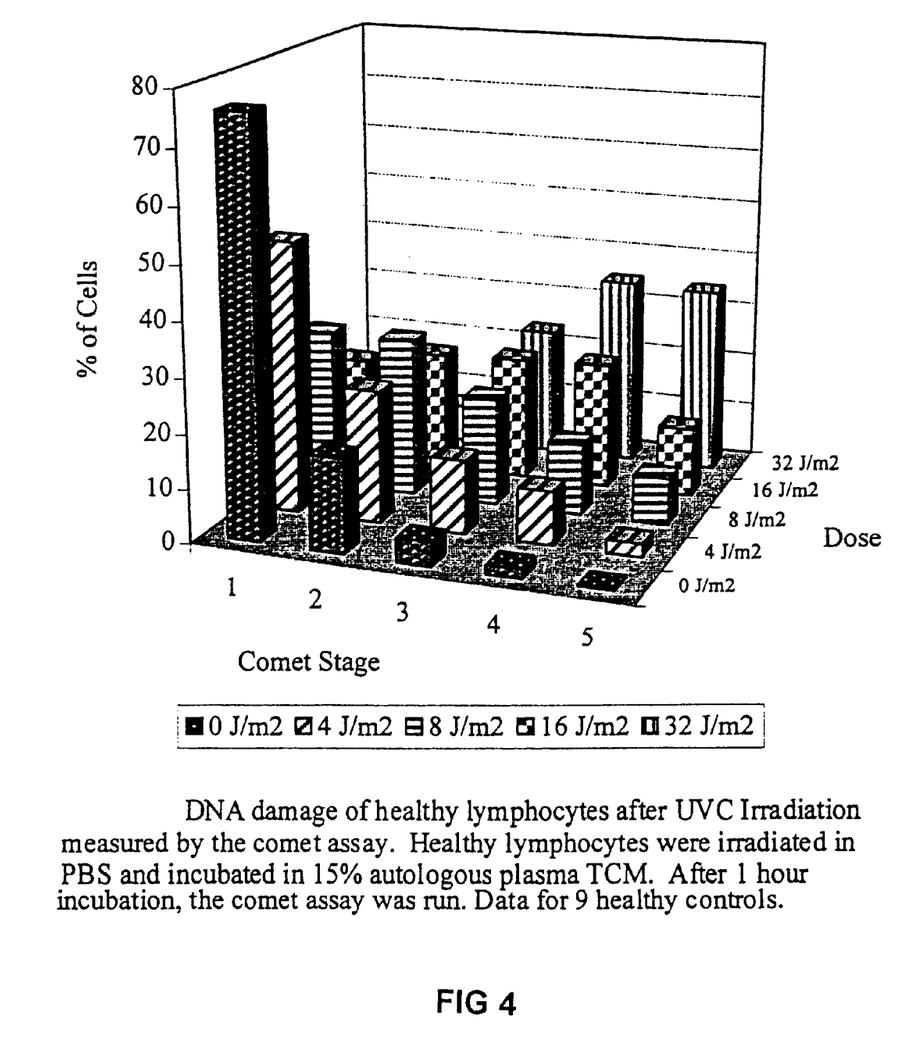

The comet assays are a measurement of single strand breaks and alkaline labile sites when the assays are run at pH's greater than 13. Comet assays are known generally in the art as referenced in the publication by Fairbairn et al, *Mutation Research*, 339, 37–59 (1995) and which is incorporated herein by reference. As seen in comparison of the CLL lymphocyte comet data in FIG. 3 with the control data in FIG. 4, it is seen that increasing amounts of UVC radiation will induce greater comet lengths for human lymphocytes, indicating greater amounts of strand breakage. For healthy control cells, there is a gradual shift in the percentage of cells exhibiting higher stages of damage with increasing UVC dose. In contrast, in cells from CLL patients, there is a dramatic increase in DNA damage even at the lowest UVC dose tested of 4 $J/m^2$. As seen in reference to FIG. 3, the unirradiated CLL cells produce comets in stage 1, but after minimal exposure to UV radiation, 73% of the cells produced comets in stages 4 and 5. The comet assay establishes the fact that following UVC irradiation, CLL lymphocytes accumulate single strand breaks to a much greater extent than healthy lymphocytes do. As discussed below, it is believed that the hypersensitivity of CLL lymphocytes to UVC radiation results from the inability of the CLL cells to complete repair of UVC-induced DNA damage. As single strand breaks accumulate, cellular activity brings about a depletion of NAD and ATP, triggering cell death by apoptotic and necrotic mechanisms.

Figure 5:
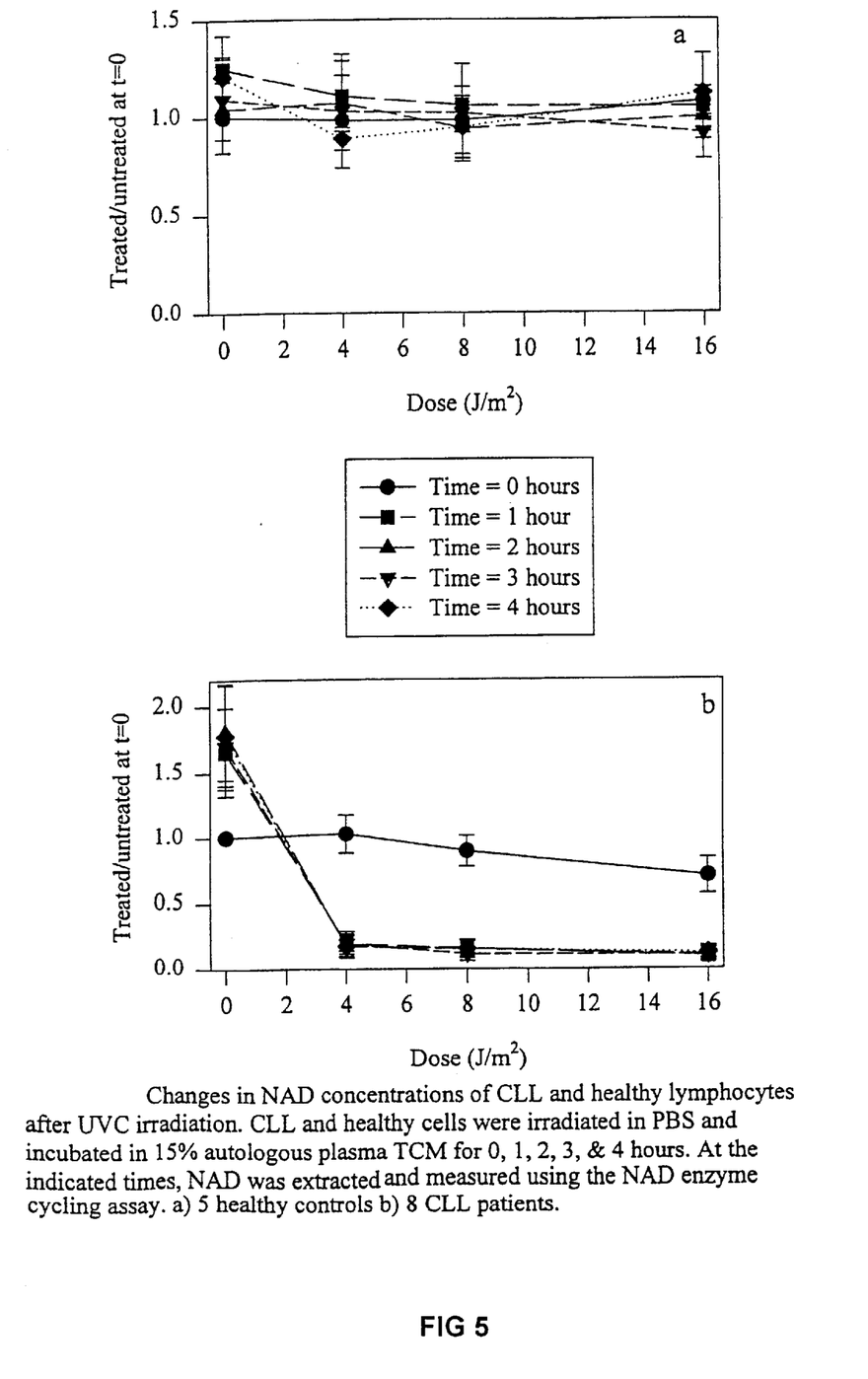
FIG. 5 sets forth graphs indicating changes in AND concentrations of CLL and healthy lymphocytes following UVC irradiation.

As seen in reference to FIG. 5, changes in NAD concentrations of CLL and healthy lymphocytes were determined following UVC irradiation. For CLL lymphocytes, there was a depletion of NAD at all doses tested. It is believed from literature reports that damage to DNA cells brings about an activation of poly (ADP-ribose) polymerase (PARP) which results in a rapid depletion of NAD following DNA damage. As indicated in FIG. 5, healthy lymphocytes exposed to low dose UVC radiation have no significant decrease in NAD concentration indicating very little PARP activation. In contrast, for CLL lymphocytes, there was depletion of NAD at all doses tested.

While not wishing to be limited by theory, it is believed that a drastic decrease in NAD as reflected above will inhibit ATP production in CLL cells. While not separately reported herein, Applicant's have measured and observed that ATP production is decreased in CLL cells exposed to UVC radiation. It is believed that the decrease in NAD and subsequent ATP production affects energy-dependent processes such as DNA, RNA, and protein synthesis. The inability of the CLL lymphocytes exposed to UVC irradiation to carry out these processes leads to the cell death of CLL lymphocytes. This observation is consistent with literature reports that GO phase CLL lymphocytes have significantly lower levels of ATP, CTP, UTP, and CDP than lymphocytes from healthy donors. Liebs et al, *Cancer Research*, 43, 5608–5617 (1983). The observation is further consistent with Applicant's unreported work that the effects of UVC radiation on CLL lymphocytes may be mitigated by supplementing the cell medium with deoxyribonucleosides. Accordingly, treatment protocols involving UVC exposure of lymphocytes should maintain lymphocytes in a non-enhanced medium.

In accordance with this invention, it has been further found that the UVC exposure to CLL lymphocytes results in cell death via a combination of apoptotic and necrotic pathways. Cells from CLL patients and healthy donors were examined for signs of apoptotic and necrotic death by flow cytometry using Annexin V and propidium iodide (PI). Annexin V binds to phosphtidylserine which appears on the outer membrane of a cell in an early stage of apoptosis. Propidium iodide is used to stain the membranepermeable population of cells.

Figure 6:
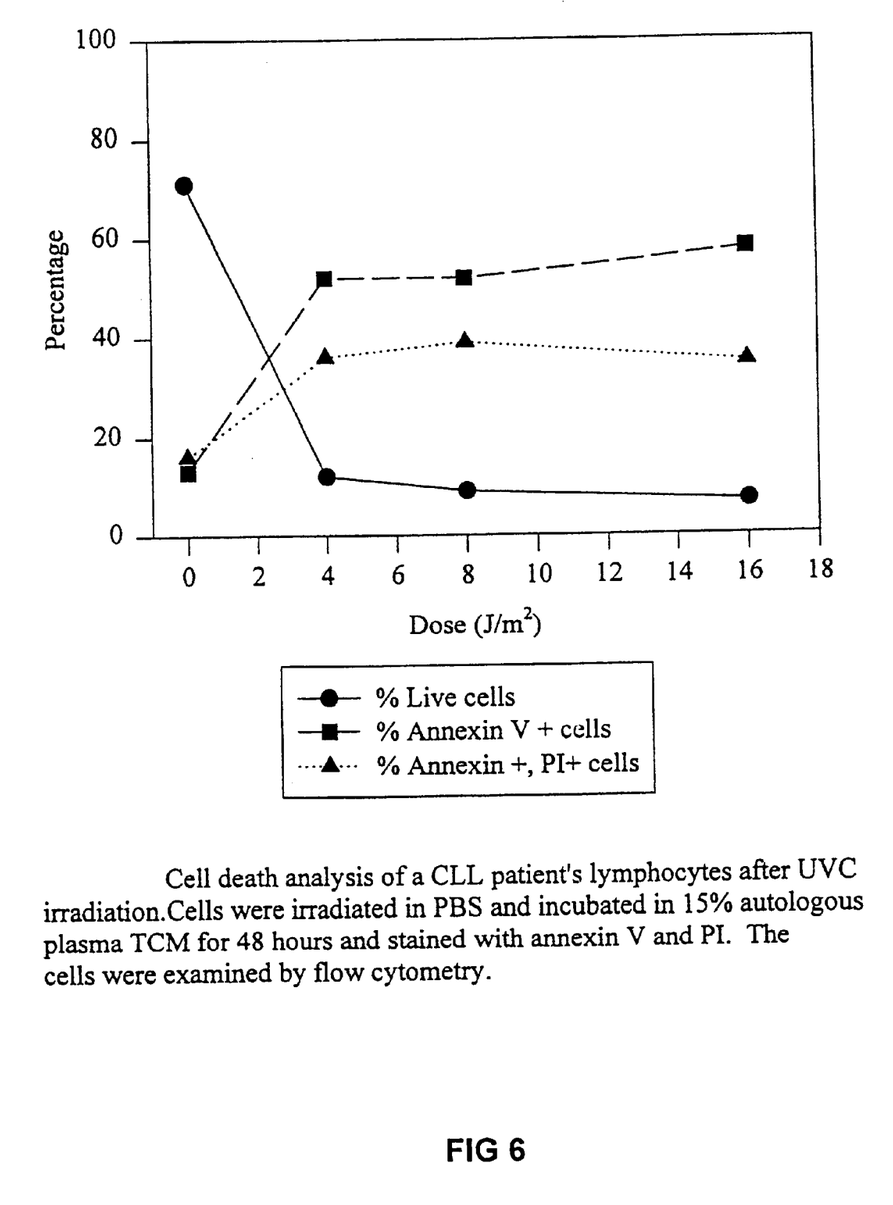
FIGS. 6–8 are graphs setting forth cell death analysis of CLL and healthy lymphocytes following UVC irradiation. Irradiated cells were incubated in 15% autologous plasma TCM for 48 hours and stained with Annexin V and PI followed by examination using flow cytometry.
Figure 7:
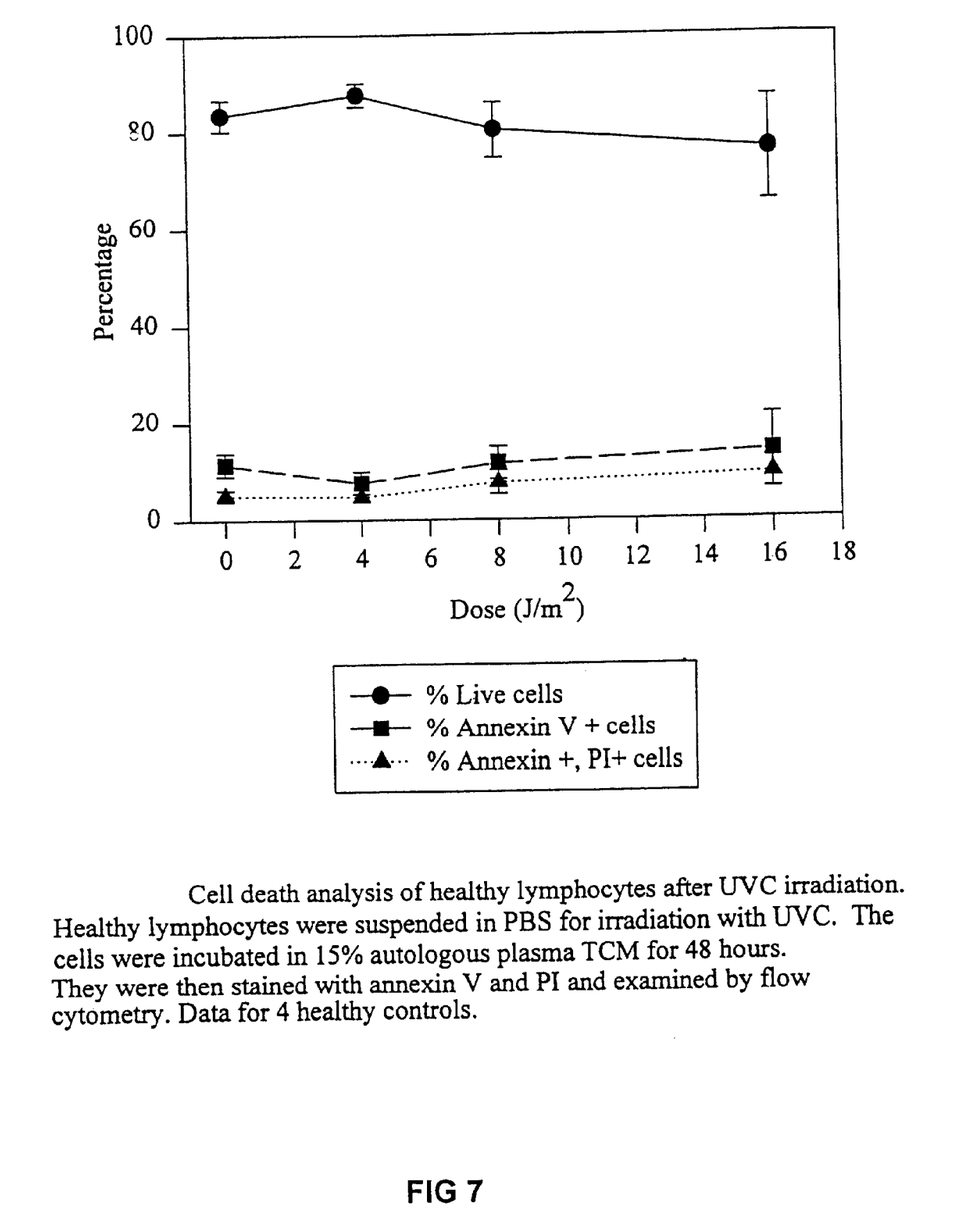
Figure 8:
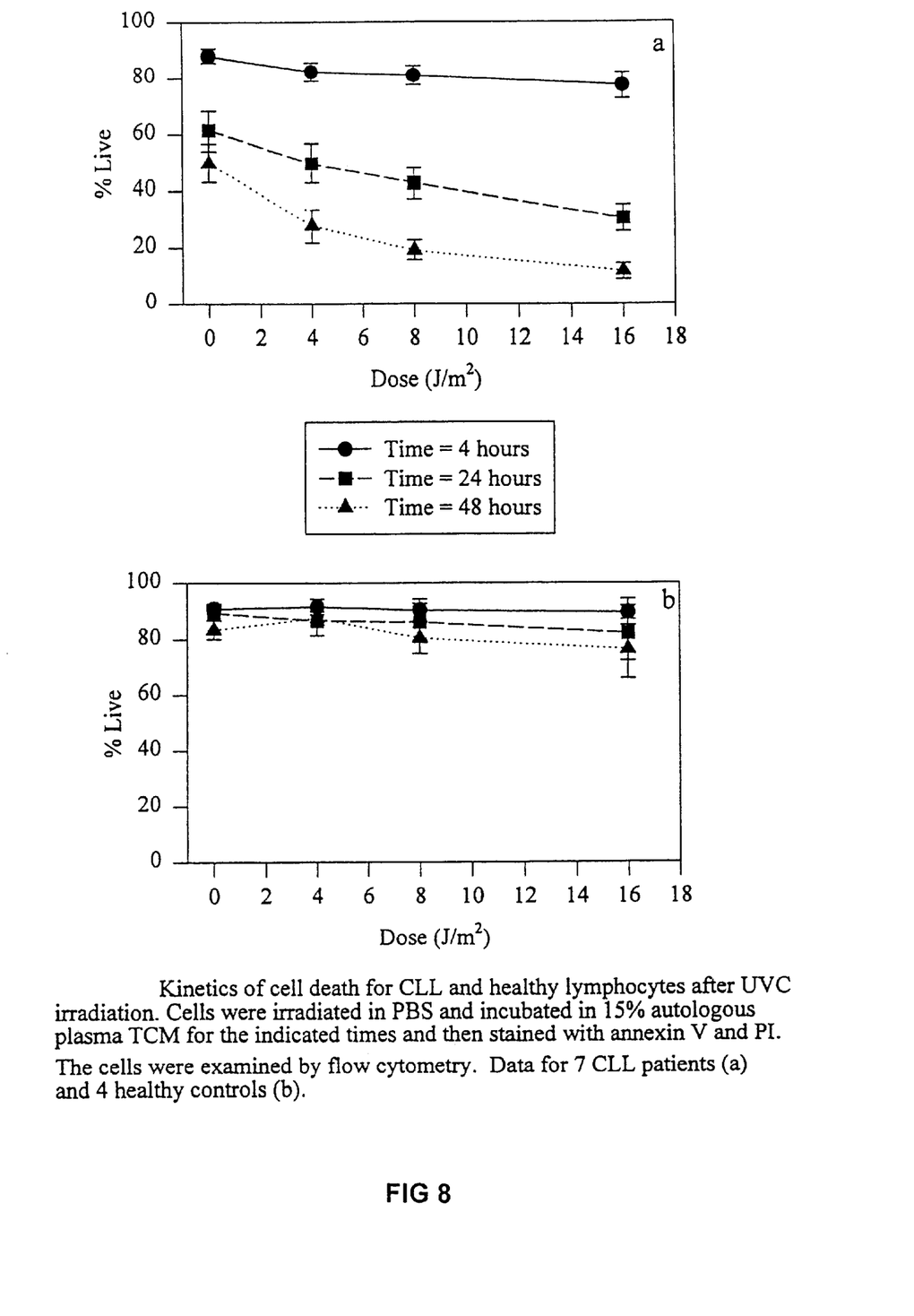

As best seen in reference to FIGS. 6–18, cells which did not stain were considered to be alive. Those cells which stained positively with Annexin V but not with Pi, were apoptotic. Those cells which stained positively for both Annexin V and PI were considered necrotic. The data in FIG. 6 is in agreement with the results of Trypan blue staining in FIG. 1, in that cells from CLL patients are significantly more sensitive to killing by UVC. It is further noted that cells having the typical apoptotic morphology characterized by condensed nuclei and smaller size were present in samples containing UVC irradiated cells from CLL patients. However, no cells exhibiting the typical apoptotic morphology were found in samples of the UV-irradiated healthy cells.

Figure 9:
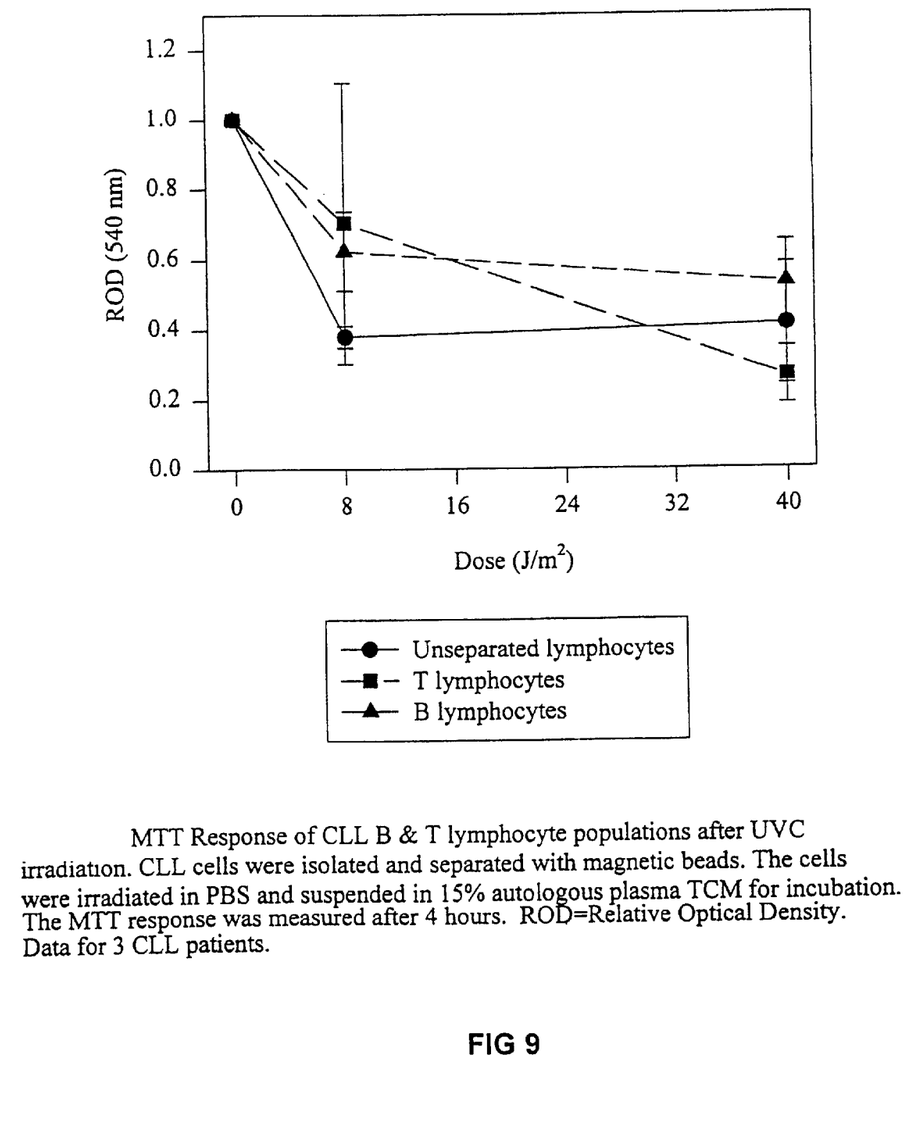
FIG. 9 is a graph of the MTT response of CLL B and T lymphocytic populations following UVC irradiation.

As set forth in FIG. 9, the sensitivity of CLL cells to UVC radiation targets both T-lymphocytes and B-lymphocytes taken from CLL patients. As seen in FIG. 9, when the populations of lymphocytes are segregated as described above to the T-lymphocyte fractions and B-lymphocyte fractions, both fractions show characteristic sensitivity to UVC irradiation as measured by the MTT response.

Based upon the above results, the heightened sensitivity to UVC radiation of lymphocytes of CLL patients provides for a therapeutic treatment process which takes advantage of the UVC sensitivity.

Figure 10:
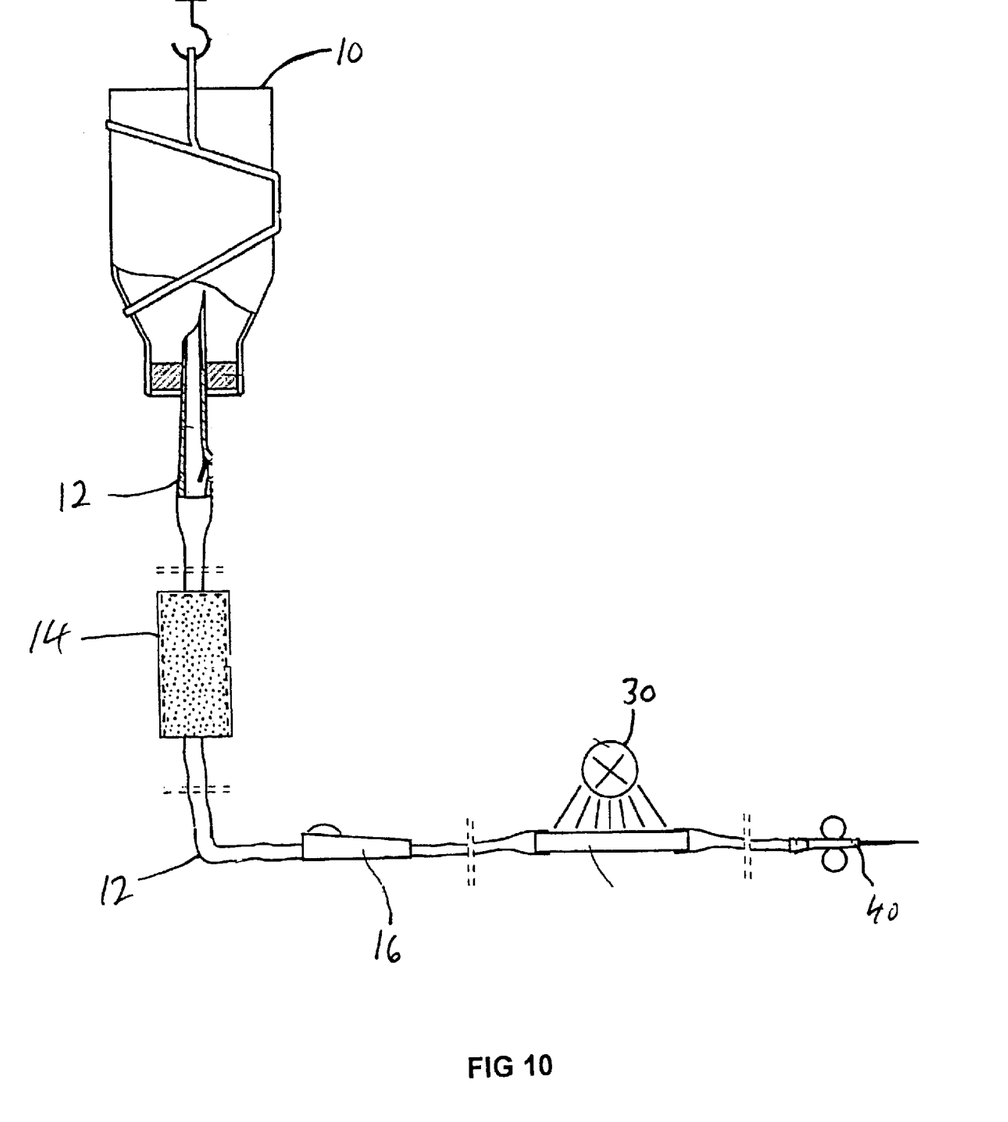
FIG. 10 is a schematic drawing illustrating a method of treating lymphocytes by exposure to UVC radiation.

One suitable treatment method and apparatus can be seen in reference to FIG. 10 in which a supply of lymphocytes is present within a container 10. Container 10 may be in the form of a conventional self-contained package of blood products or may be part of a continuous supply conduit from a continuous centrifuge blood treatment apparatus. As further seen in reference to FIG. 10, the lymphocyte fraction flows through tubing 12 and may pass through an optional filter 14. An optional roller clamp 16 may be provided for pinching off the conduit tubing 12.

Conduit 12 is in communication with a first end of a quartz tube 20 in which there is a UVC light source 30. As the cells flow through quartz tube 20, the cells are irradiated by the UVC light source 30. Preferably, the emission of the UVC radiation occurs between about 250 to about 270 nm, and more preferably at the wavelength of 254 nm. The preferred irradiation doses received by the CLL lymphocytes are between 1 to 40 J/m$^2$ and more preferably between about 2 to 24 J/m$^2$ and still more preferably between the range of about 4 to 10 J/m$^2$.

In the method according to the present invention, the irradiation doses and the wavelength used are chosen so that the irradiation doses received by the CLL lymphocytes affect the nucleic acids of the CLL lymphocytes with minimal disruption of the structure of the peptides or proteins present in the lymphocytes or associated plasma. While the example referenced above uses a quartz tube through which the cells are illuminated, other structures such as tubing, bags, glass plates, and other structures may be used. Preferably, the illumination window should be constructed of materials which do not absorb UVC radiation.

Following treatment, the treated lymphocytes are removed from a second end of the quartz tube 20 where they may be re-introduced to the patient through a cannula 40.

The advantage of the present treatment protocol is that a significant portion of the affected CLL cells undergo an apoptopic cell death. As such, the amount of adverse immune reaction associated with the necrotic death pathway is reduced. As such, a larger volume of a patient's lymphocytes may be treated at any one time than if all the affected cells underwent an necrotic death.

While it is preferred that initial treatments involve 10% of a patient's total lymphocytes at any one interval, the amount may be varied depending upon the patient's subsequent response and tolerance to the treatment process.

It should be appreciated that the present invention does not require the use of any photoactive agents or chemical treatments to bring about the death of the CLL lymphocytes. However, it may be possible to combine the present UVC treatment of CLL lymphocytes with other conventional drug therapies so as to enhance the treatment of a patient.

It is also understood that the UVC light is but one agent that may be used to bring about a threshold level of DNA damage to CLL lymphocytes. Other combinations of light wavelengths, drugs, heat treatments, or other processes which bring about DNA damage may, in accordance with this invention, achieve similar results. For instance, any treatment process which brings about an equivalent damage to the CLL lymphocyte's DNA may be expected to achieve similar mortality of the CLL cells given the demonstrated inability of CLL cells to undergo repair following damage to the nucleic acids. However, use of UVC light as the initiating agent is preferred in that there have been no observed side effects or detrimental results to healthy lymphocytes.

It is also noted that the preferred range of UVC irradiation levels are significantly lower than the ranges used in the past to treat bacterial and/or viral contaminants in excorporeal treatment systems. Applicant's present invention has recognized and demonstrated that the CLL lymphocytes have an enhanced sensitivity to UVC irradiation which allows the selective destruction of the CLL lymphocytes without compromising the health and viability of non-CLL lymphocytes and other cell tissue types.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole or in part. Therefore, the spirit and scope of the appended claims should not be limited to the description of the preferred versions contained therein.

That which is claimed is:

1. A method for reducing the population of lymphocytes from chronic lymphocytic leukemia patients comprising:

withdrawing blood from a patient; and, passing a blood product comprising a separated population of lymphocytes removed from a CLL patient past a type C ultra-violet radiation source such that the irradiation dose of ultra-violet radiation received by the lymphocytes is within the range of about 1 to about 40 joules/m$^2$.

2. The method according to claim 1 wherein the irradiation dose of UVC radiation received by the lymphocytes is between about 1 to about 12 joules/m$^2$.

3. The method according to claim 2 wherein the irradiation dose of UVC radiation is between about 2 to about 10 joules/m$^2$.

4. The method according to claim 1 wherein the UVC radiation occurs at a wavelength around 254 nm.

5. A process of killing lymphocytes from a patient having chronic lymphocytic leukemia comprising the steps of:

removing a supply of lymphocytes from a CLL patient;

irradiating said supply of lymphocytes with UVC radiation so that said cells receive an effective amount of UVC radiation so as to initiate a cell death process; and, returning the irradiated lymphocytes to the patient.

6. The process according to claim 5 comprising the additional step of maintaining said irradiated supply of lymphocytes in a medium lacking supplemental deoxyribonucleosides.

7. A method for reducing the population of accumulated B-lymphocytes in the G0 stage of a cell cycle from a chronic lymphocytic leukemia patient comprising the steps of:

withdrawing blood from said patient;

treating said withdrawn blood so as to provide a separated population of blood comprising lymphocytes;

irradiating said population of lymphocytes with UVC radiation so that said cells receive an effective amount of UVC radiation so as to initiate a cell death process; and, returning said treated lymphocyte supply to said patient wherein the treated lymphocytes die.

8. The method according to claim 7 comprising the additional step of maintaining said irradiated population of lymphocytes in a medium lacking supplemental deoxyribonucleosides.

9. The method according to claim 1 comprising the additional step of maintaining the irradiated lymphocytes in a medium lacking supplemental deoxyribonucleosides.

10. The method according to claim 7 wherein said UVC radiation occurs at a wavelength of about 254 nm.

11. The method according to claim 7 wherein the effective amount of UVC radiation is between about 1 to about 12 joules/m$^2$.

12. The method according to claim 7 wherein said effective amount of UVC radiation is between about 2 to about 10 joules/m$^2$.

* * * * *